United States Patent [19]
Nomura

[11] Patent Number: 5,618,272
[45] Date of Patent: Apr. 8, 1997

[54] INTRAVENOUS CATHETER SET

[75] Inventor: Shoemon Nomura, Chiba, Japan

[73] Assignee: Kabushiki-Kaisha Median, Tokyo, Japan

[21] Appl. No.: 642,995

[22] Filed: May 6, 1996

Related U.S. Application Data

[63] Continuation-in-part of Ser. No. 385,867, Feb. 9, 1995, abandoned.

[30] Foreign Application Priority Data

Nov. 30, 1994 [JP] Japan .................................. 6-321599

[51] Int. Cl.⁶ .................................................. A61M 5/00
[52] U.S. Cl. .......................................... 604/166; 604/161
[58] Field of Search ................................. 604/161, 163, 604/165, 166, 164, 157, 158, 264, 274

[56] References Cited

U.S. PATENT DOCUMENTS

| | | | |
|---|---|---|---|
| 3,030,953 | 4/1962 | Koehn | 604/166 |
| 3,082,769 | 3/1963 | Palmer | 604/166 |
| 3,388,703 | 6/1968 | Bowes | 604/166 |
| 3,612,050 | 10/1971 | Sheridan | 604/166 |
| 3,788,326 | 1/1974 | Jacobs | 604/161 X |
| 4,147,165 | 4/1979 | Tauschinski | 604/161 |
| 4,411,655 | 10/1983 | Schreck | 604/165 |
| 4,645,491 | 2/1987 | Evans | 604/161 X |
| 4,964,854 | 10/1990 | Luther | 604/166 |
| 4,995,866 | 2/1991 | Amplatz et al. | 604/166 X |

*Primary Examiner*—Sam Rimell
*Attorney, Agent, or Firm*—Lowe, Price, LeBlanc & Becker

[57] ABSTRACT

An intravenous catheter set includes a needle 1, having a proximal end 5 and a distal end 3 and a catheter 2, in which the needle 1 is detachably inserted in such a manner that the sharpened end 3 of the needle 1 extends from a front end of the catheter 2, which has a front end equal to or slightly smaller in outer diameter than the distal end 3 which forms a sharpened end, and which has its base end gradually reduced in diameter rearward to form a reduced-diameter portion 4 with a tapered surface 4a. Portion 4 is followed by the proximal end 5 which gradually increases in diameter rearwardly to form a tapered portion 5 corresponding in shape to a front end 7 of the catheter 2, to minimize the resistance of a blood vessel's wall against the catheter 2 in piercing the vessel's wall with the needle and to substantially prevent a front end of the catheter 23 from rolling back or tearing. The catheter tube is constructed of polyetherblock amide in which polyamide-blocks and polyetherblocks are alternately arranged and linearly combined with each other.

1 Claim, 3 Drawing Sheets

INTRAVENOUS CATHETER SET

RELATED APPLICATION

This application is a continuation-in-part of my application Ser. No. 08/385,867, filed Feb. 9, 1995, abandoned, and entitled "Intravenous Catheter Set".

BACKGROUND OF THE INVENTION

1. Field of the Invention

The present invention relates to an intravenous catheter set that is used in medical treatment, for example, in drip infusion, in blood transfusion, in dialysis and in like treatments.

2. Description of the Prior Art

A catheter tube of an intravenous catheter set is inserted into a blood vessel of a patient so that, through such catheter tube, a necessary medical treatment such as: injection of a medicine into the patient's blood vessel; continuous administration of nutriment to the patient; blood transfusion and/or dialysis necessary for the patient; and like treatments is conducted.

The catheter tube of a conventional type is constructed of a polytetrafluoroethylene tube or a polyurethane tube having an outer diameter of, for example, from 0.7 to 2.1 mm and an inner diameter of from 0.5 to 1.7 mm. It is not possible for the catheter tube by itself to enter the blood vessel.

Consequently, an inner needle member, which enables the catheter tube to enter the blood vessel, is detachably mounted in a front-end portion of the catheter tube in an insertion manner. The needle member is constructed of a hollow metallic tube having an outer diameter of from 0.5 to 1.7 mm, and extends from a front end of the catheter tube so as to pierce a wall of the blood vessel.

The needle member pierces the blood vessel's wall to enable the catheter tube to enter the blood vessel. After the catheter tube enters the blood vessel, the needle member is removed from (i.e., pulled out of) the catheter tube so that only the catheter tube remains or indwells in the blood vessel.

As described above, in the intravenous catheter set, the catheter tube is provided with the inner needle member therein, and is, therefore, naturally larger in diameter than the needle member. A conventional type of the inner needle member is constructed of a straight tube with a sharpened end forming a knife portion. Consequently, in a condition in which the needle member is mounted in the catheter tube in an insertion manner, as shown in FIG. 6, a front-end surface (i.e., cross sectional area) 12a of the wall of the catheter tube 12 forms an annular shoulder portion which extends radially outwardly from an outer peripheral surface of the needle member 11. When the needle member pierces the wall of the blood vessel, such shoulder portion or front-end surface 12a of the catheter tube 12 is resistant to the insertion of the catheter tube into the blood vessel.

Since the catheter tube is thin in thickness of the wall, it tends to have its front-end portion rolled back due to the presence of its shoulder portion 12a which abuts against the blood vessel's wall when the wall is pierced by the needle member 11. The thus rolled-back front-end portion of the catheter tube 12 is further enlarged in diameter and/or is torn, thus inflicting bodily and mental pain on the patient. Sometimes, the blood vessel is badly damaged by such diametrically enlarged and/or torn front-end portion of the catheter tube 12, which makes it difficult to continue the medical treatment of the patient.

Further, in piercing of the muscles and the wall of the blood vessel of the patient with the needle member of the catheter set, these muscles and blood vessels contract to increase their resistance to the shoulder portion 12a of the catheter tube 12, which facilitates rolling-back and/or tearing the front-end portion of the catheter tube 12.

Further, since the catheter tube made of polytetrafluoroethylene is poor in softness and flexibility, an inner wall of the patient's blood vessel is often damaged by the catheter tube and suffers from thrombophlebitis when the catheter tube is inserted into the patient's blood vessel. Furthermore, for example, in case that the catheter tube remains or indwells in the blood vessel of the patient's arm, there is a fear that the catheter tube may be broken when the patient bends his arm.

On the other hand, as for a catheter tube made of polyurethane, it is good in softness and flexibility but poor in smoothness. Consequently, a catheter tube made of polyurethane often permits the thrombocyte (i.e., blood platelet) to adhere to a surface of the catheter tube to produce the thrombus inside the blood vessel.

In a clinical test, it has been recognized that an allowable remaining (i.e., indwelling) time period for the catheter tube made of polytetrafluoroethylene in the blood vessel is 24 hours at maximum, and that of the catheter tube made of polyurethane is 48 hours at maximum.

Further, a surface in any of the catheter tubes made of polytetrafluoroethylene and that made of polyurethane is large in frictional resistance, and therefore gives the patient considerable pain when the catheter tube is inserted into the patient's blood vessel. Furthermore, it takes too much time and labor to pull the inner needle member out of the catheter tube due to its large pull-out resistance.

In the prior art, silicones are applied to the surface of the catheter tube to reduce its frictional resistance. However, nowadays, silicones have been found to be carcinogenic and are therefore prohibited from being applied to any medical instruments.

SUMMARY OF THE INVENTION

It is an object of the present invention to provide an intravenous catheter set, which is safe in use and free from any fear of rolling-back and tearing of a front-end portion of a catheter tube of the catheter set.

More particularly, the following objects are accomplished by providing the catheter set of the present invention:

(a) A resistance of the catheter set encountered when it is inserted into the blood vessel is reduced;

(b) A pull-out resistance of the inner needle member of the catheter set encountered when the needle member is pulled out of the catheter tube is reduced;

(c) Consequently, it is possible to use the catheter set safely without giving the patient considerable pain and fear;

(d) It is possible to have the patient's blood vessel be free from the thrombophlebitis since the catheter set substantially does not damage the inner wall of the patient's blood vessel; and (e) The surface of the catheter tube is less prone to adhesion to blood platelet, which increases the allowable remaining (i.e., indwelling) time period for the catheter tube in the blood vessel.

According to an aspect of the present invention, the above object of the present invention is accomplished by providing:

An intravenous catheter set comprising:

an inner needle member constructed of a hollow metallic tube having an axial lumen, a proximal end and a distal end, the distal end being obliquely cut to form a sharpened-end portion which has its base portion gradually reduced in diameter rearward to form a reduced-diameter portion provided with a tapered surface, the reduced-diameter portion being followed by the proximal end forming a tapered portion which is gradually increased in diameter rearward; and a catheter tube constructed of a plastic tube having its front-end portion tapered so as to correspond to the tapered portion of the inner needle member, which member is detachably mounted in the catheter tube in an insertion manner and in a manner such that the sharpened-end portion of the inner needle member extends from a front end of the catheter tube, the catheter tube having its front-end portion equal in outer diameter to the distal end of the needle member, said catheter tube being constructed of polyether-block amide in which polyamide-blocks and polyether-blocks are alternately arranged and linearly combined with each other.

DESCRIPTION OF THE PREFERRED EMBODIMENTS

Hereinbelow, the present invention will be described in detail with reference to the accompanying drawings.

Figure 1:
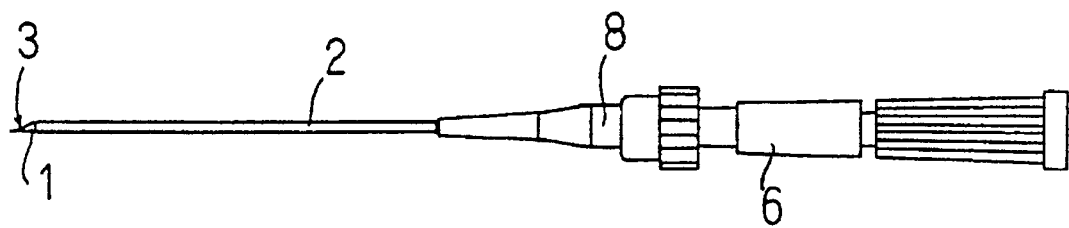
FIG. 1 is a schematic view of the intravenous catheter set of the present invention.
Figure 2:
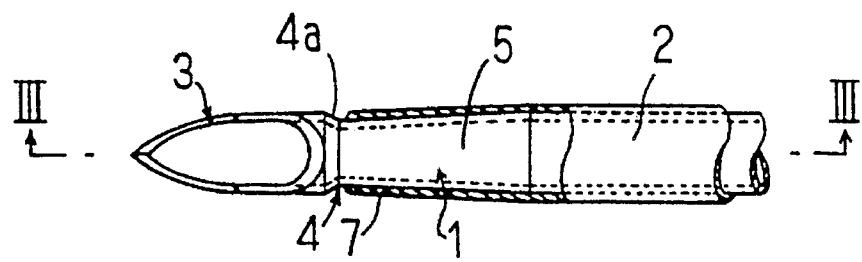
FIG. 2 is an enlarged view of an essential part of the intravenous catheter set of the present invention shown in FIG. 1.
Figure 3:
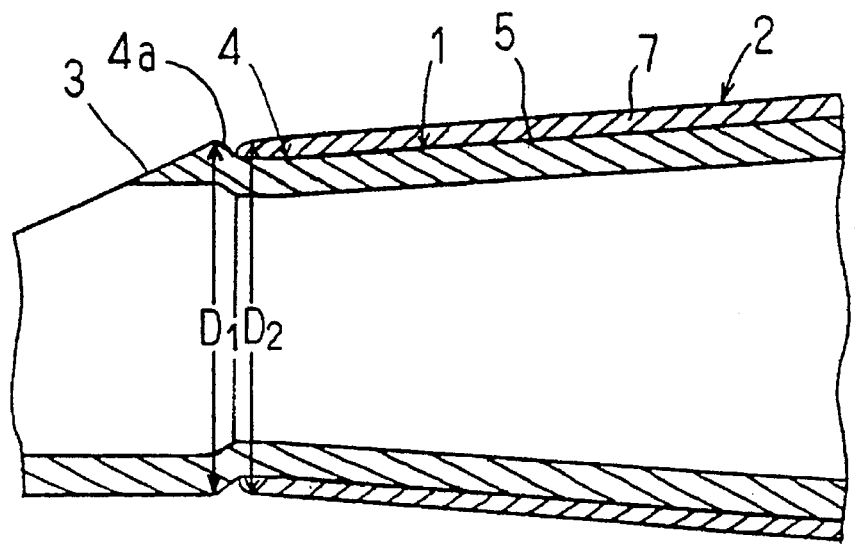
FIG. 3 is a further-enlarged sectional view of the essential part of the intravenous catheter set of the present invention, taken along the line III—III of FIG. 2.
Figure 4:
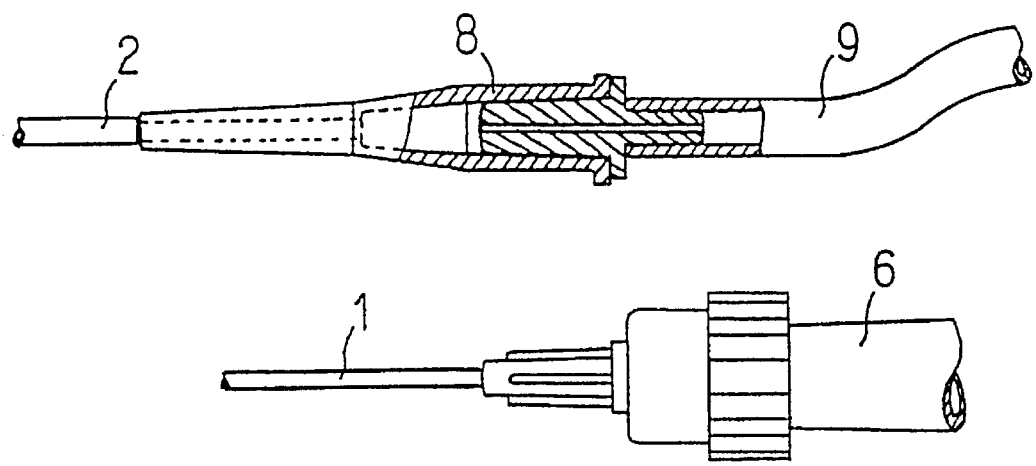
FIG. 4 is a view showing a condition in which the inner needle member is removed from the catheter tube, and a liquid-delivery tube is connected with the catheter tube.

In FIGS. 1 to 3 an inner needle member of an intravenous catheter set of the present invention is denoted by a reference numeral 1 and a catheter tube is denoted by a reference numeral 2. The inner needle member 1 is detachably mounted in a front-end portion of the catheter tube 2 in an insertion manner.

In the intravenous catheter set of the present invention, the inner needle member 1 is constructed of a hollow metallic tube having an axial lumen, a proximal end and a distal end. The distal end of the inner needle member 1 is obliquely cut to form a sharpened-end portion or knife portion 3, and has its base end formed into a reduced-diameter portion 4 which is constructed of a tapered surface 4a gradually reduced in diameter rearward following the tapered surface 4a. In the inner needle member 1, its proximal end following the reduced-diameter portion 4 is gradually increased in diameter rearward to form a tapered portion 5 which has its base portion mounted in a holder 6.

The catheter tube 2 is constructed of polyether-block amide in which polyamide-blocks and polyether-blocks are alternately arranged and linearly combined with each other to form the polyether-block amide, as illustrated by the following chemical formula:

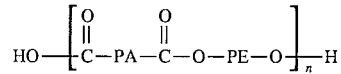

This polyether-block amide is good in any of toughness, softness, flexibility and resiliency and, in addition, is excellent in smoothness and low in frictional resistance.

The catheter tube 2 has its front-end portion 7 tapered so as to correspond to the tapered portion 5 of the inner needle member 1. A rigid base-sleeve member 8 following the catheter tube 2 is connected with a liquid-delivery tube such as drip infusion tubes.

The inner needle member 1 has its tapered portion 5 detachably mounted in the thus tapered corresponding front-end portion of the catheter tube 2 in a manner such that: the sharpened-end portion 3 of the inner needle member 1 extends from the front end of the catheter tube 2; and, the catheter tube 2 has an outer diameter $D_2$ of its front end equal to an outer diameter $D_1$ of the base end of the sharpened-end portion 3 of the needle member 1.

In other words, the reduced-diameter portion 4 of the inner needle member 1 is smaller in outer diameter than the base end of the sharpened-end portion 3 of the inner needle member 1 by an amount of a thickness of a wall of the catheter tube 2.

The intravenous catheter set of the present invention has the above construction, and is used in a condition in which the inner needle member 1 is detachably mounted in the catheter tube 3 in an insertion manner to have its sharpened-end portion 3 extended forwardly from the front end of the catheter tube 2.

Although an outer diameter of the base portion of the sharpened-end portion 3 of the inner needle member 1 is slightly larger than an inner diameter of the catheter tube 2, since the catheter tube 2 is made of a polyether-block amide, it is possible for the inner needle member 1 to smoothly enter the catheter tube 2. Further, in a condition in which the sharpened-end portion 3 of the inner needle member 1 extends forward from the front end of the catheter tube 2, such front end of the catheter tube 2 firmly fits to the reduced-diameter portion 4 of the inner needle member 1 due to its resiliency.

Under such circumstances, a blood vessel's wall of a patient is pierced by the sharpened-end portion 3 of the inner needle member 1 to permit the front-end portion 7 of the catheter tube 2 to enter the patient's blood vessel.

Since the front end of the catheter tube 2 is equal in outer diameter to the base end of the sharpened-end portion 3 of the inner needle member 1, the resistance of the blood vessel's wall against the front end of the catheter tube 2 is minimized when the inner needle member 1 pierces the wall of the patient's blood vessel, which permits the inner needle member 1 to smoothly enter the blood vessel to substantially prevent the front-end portion of the catheter tube 2 from rolling back or tearing.

After completion of insertion of the catheter tube 2 into the blood vessel, the inner needle member 1 is pulled back and removed from the catheter tube 2. At this time, since the tapered surface 4a of the reduced-diameter portion 4 of the base end of the sharpened-end portion 3 is reduced in diameter in the rearward direction, there is no fear that the tapered surface 4a of the reduced-diameter portion 4 may engage with the front-end surface of the catheter tube 2 and prevent the inner needle member 1 from being pulled back and removed from the catheter tube 2. Consequently, it is possible to easily remove the inner needle member 1 from the catheter tube 2. Thereafter, the base-sleeve member 8 of the catheter set is connected with a liquid-delivery tube 9 such as those used in drip infusion, liquid-medicine injection, blood transfusion, dialysis and like medical treatments for injecting nutriment, liquid medicines, blood and like beneficial agents into the patient's blood vessel. In case of dialysis, the blood circulates through both the patient's body and a dialyzer.

In operation, the inner needle member 1 pierces the wall of the patient's blood vessel so that both the inner needle member 1 and the catheter tube 2 are introduced into the blood vessel. At this time, since the inner needle member 1 is provided with the reduced-diameter portion 4 in its base end of the sharpened-end portion 3 and the portion 4 is followed by the tapered portion 5 which is increased in diameter rearward, and since the front-end portion 7 of the catheter tube 2 is reduced in diameter forward or tapered so as to correspond to the tapered portion 5 of the inner needle member 1, the front end of the catheter tube 2 is equal in outer diameter to the base end of the sharpened-end portion 3 of the inner needle member 1.

Consequently, in piercing the blood vessel's wall with the sharpened-end portion 3 of the inner needle member 1, the resistance of the front-end surface of the catheter tube 2 against the blood vessel's wall is minimized to permit both the inner needle member 1 and the catheter tube 2 to smoothly enter the blood vessel of the patient.

Figure 5:
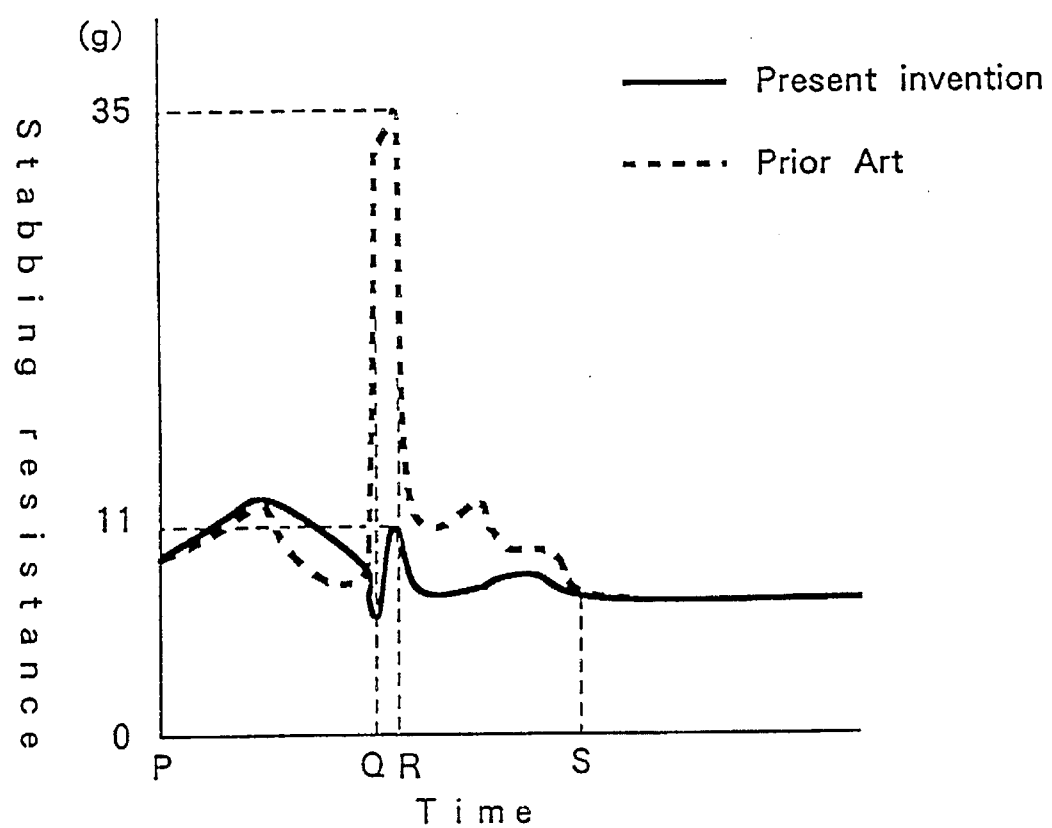
FIG. 5 is a graph illustrating the test results in a sharpness test of the intravenous catheter set of the present invention.
Figure 6:
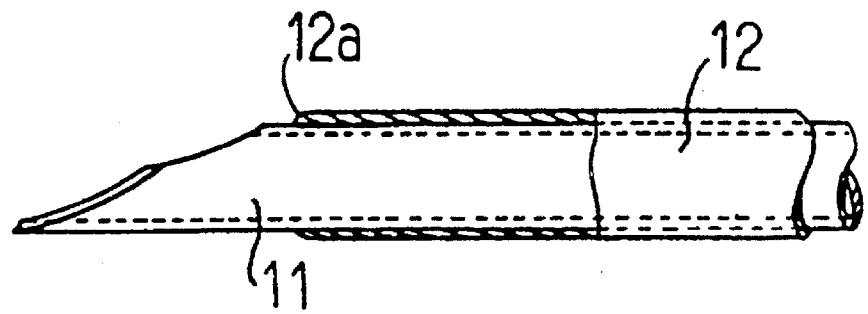
FIG. 6 is a partially sectional view of an intravenous catheter set of a conventional type.

The graph shown in FIG. 5 shows the results of a sharpness test of a catheter tube of a size of 20 G (i.e., outer diameter of 1.1 mm) in the intravenous catheter set of the present invention, the test results being indicated in solid line. On the other hand, the results of the same sharpness test of a catheter tube of the same size of 20 G in a conventional intravenous catheter set shown in FIG. 6 are shown in FIG. 5 in dotted line. Consequently, in the graph shown in FIG. 5, the catheter tube of the present invention and that of the conventional type are compared with each other in stabbing resistance.

In the same graph shown in FIG. 5, the vertical (y) axis shows the stabbing resistance, and the horizontal (x) axis indicates time, in which: "P-Q" shows a period of time in piercing the blood vessel's wall with the sharpened-end portion 3 of the inner needle member 1; "Q-R" indicates a period of time in piercing the blood vessel's wall with the front end of the catheter tube 2; and "R-S" indicates a period of time in piercing the blood vessel's wall with the front-end portion 7 of the catheter tube 2.

This graph shows that: a stabbing resistance of the conventional intravenous catheter set during the period of time "Q-R" is 35 g; and that of the intravenous catheter set of the present invention during the same period of time "Q-R" is 11g which is only one third of the stabbing resistance of the conventional set.

As is clear from the results of the sharpness tests described above, it is possible for both the inner needle member 1 and the catheter tube 2 of the intravenous catheter set of the present invention to easily pierce the wall of the patient's blood vessel. Therefore, the intravenous catheter set of the present invention is substantially free from any troubles inherent in the conventional intravenous catheter set, i.e., free from rolling-back and/or tearing of the front end of the catheter tube.

Consequently, it is possible to introduce the catheter tube of the intravenous catheter set of the present invention into the patient blood vessel in safety without inflicting physical and/or mental pain on the patient.

Further, since the catheter tube is constructed of polyether-block amide in which polyamide-blocks and polyether-blocks are alternately arranged and linearly combined with each other to form the polyether-block amide, such catheter tube is good in any of toughness, softness, flexibility and resiliency. In addition, since the surface of this catheter tube is considerably smaller in frictional resistance than that of the catheter tube made of polytetrafluoroethylene or made of polyurethane.

Consequently, when the inner needle member is pulled out of the catheter tube 2, it is possible for the inner needle member to smoothly enlarge the front-end portion of the catheter tube 2 without engaging with the front-end portion and to smoothly enter the interior of the catheter tube 2, because the catheter tube 2 is soft and flexible, and the inner needle member has the base portion of its sharpened-end portion 3 followed by the tapered surface 4a. Further, since the base portion of the sharpened-end portion 3 is brought into contact with the catheter tube 2 with a minimum contact area, a pull-out resistance of the inner needle member is small, which permits the doctor to save much time and labor in operation.

Further, since the surface of the catheter tube of the present invention is small in frictional resistance, it is possible for the doctor to safely use the catheter set of the present invention to his patient with a minimum pain without applying any silicone to the surface of the catheter tube according to the present invention, in contrast with the conventional catheter set.

Further, since the catheter tube made of polyether-block amide is soft and flexible, such catheter tube is less prone to damage an inner wall of the blood vessel, which prevents the thrombophlebitis from occurring in the inner wall of the blood vessel. In addition, since the surface of the catheter tube of the present invention is excellent in smoothness, the blood platelet is less prone to adhere to such surface of the catheter tube, which permits the catheter tube of the present invention to remain or dwell in the blood vessel for a long period of time of at least 72 hours without any fear of breakage of the catheter tube in the blood vessel.

I claim:

1. An intravenous catheter set comprising:

an inner needle member constructed of a hollow metallic tube having an axial lumen, a proximal end and a distal end, said distal end being obliquely cut to form a sharpened-end portion which has its base portion gradually reduced in diameter rearward to form a reduced-diameter portion provided with a tapered surface, said reduced-diameter portion being followed by said proximal end formed into a tapered portion which is gradually increased in diameter rearward; and a catheter tube constructed of a plastic tube having its front-end portion tapered so as to correspond to said tapered portion of said inner needle member, which member is detachably mounted in said catheter tube in an insertion manner and in a manner such that said sharpened-end portion of said inner needle member extends from a front end of said catheter tube, said catheter tube having its front-end portion substantially equal in outer diameter to said distal end of said needle member, said catheter tube being constructed of polyether-block amide in which polyamide-blocks and polyether-blocks are alternately arranged and linearly combined with each other.

* * * * *